United States Patent [19]

Leveen

[11] 4,095,602

[45] Jun. 20, 1978

[54] MULTI-PORTAL RADIOFREQUENCY GENERATOR

[76] Inventor: Harry H. Leveen, 800 Poly Pl., Brooklyn, N.Y. 11209

[21] Appl. No.: 726,843

[22] Filed: Sep. 27, 1976

Related U.S. Application Data

[63] Continuation-in-part of Ser. No. 686,300, May 14, 1976.

[51] Int. Cl.$^2$ ............................................. A61N 1/40
[52] U.S. Cl. .................................... 128/413; 128/404; 128/422
[58] Field of Search ................... 128/404, 413, 419 R, 128/420 R, 420 A, 421, 422, 423 R, 423 W, 1.3-1.5

[56] References Cited

U.S. PATENT DOCUMENTS

| | | | |
|---|---|---|---|
| 1,752,632 | 4/1930 | Beaumont et al. | 128/420 X |
| 2,838,672 | 6/1958 | Paust | 128/420 X |
| 3,646,940 | 3/1972 | Timm et al. | 128/421 |
| 3,851,651 | 12/1974 | Icenbice, Jr. | 128/422 |
| 3,895,639 | 7/1975 | Rodler | 128/422 |
| 4,019,518 | 4/1977 | Maurer et al. | 128/419 R |

FOREIGN PATENT DOCUMENTS

| | | | |
|---|---|---|---|
| 2,222,844 | 11/1973 | Germany | 128/420 |
| 2,437,346 | 2/1975 | Germany | 128/421 |

Primary Examiner—Robert W. Michell
Assistant Examiner—Lee S. Cohen
Attorney, Agent, or Firm—Henry W. Foulds, Jr.

[57] ABSTRACT

A unique apparatus for multi-portal administration of radiofrequency range electromagnetic energy for therapeutic treatment of interior portions of various substrates including animals and humans which comprises an R.F. signal generator which is connected to a timer component having switching logic to apply R.F. electromagnetic energy one set at a time, sequentially across a plurality of sets of paired electrode plates, i.e., applicators. Each set of paired electrode plates is positioned on a different axis with reference to a fixed central point located between the plates at which such axes approximately intersect and which is the location of the portion to be treated.

The apparatus permits a fixed target, i.e., portion to be treated, to receive a constant input of R.F. energy although such energy is coming from different directions and emanating from different electrodes, hence several R.F. fields are created sequentially by the control mechanism as it functions.

4 Claims, 2 Drawing Figures

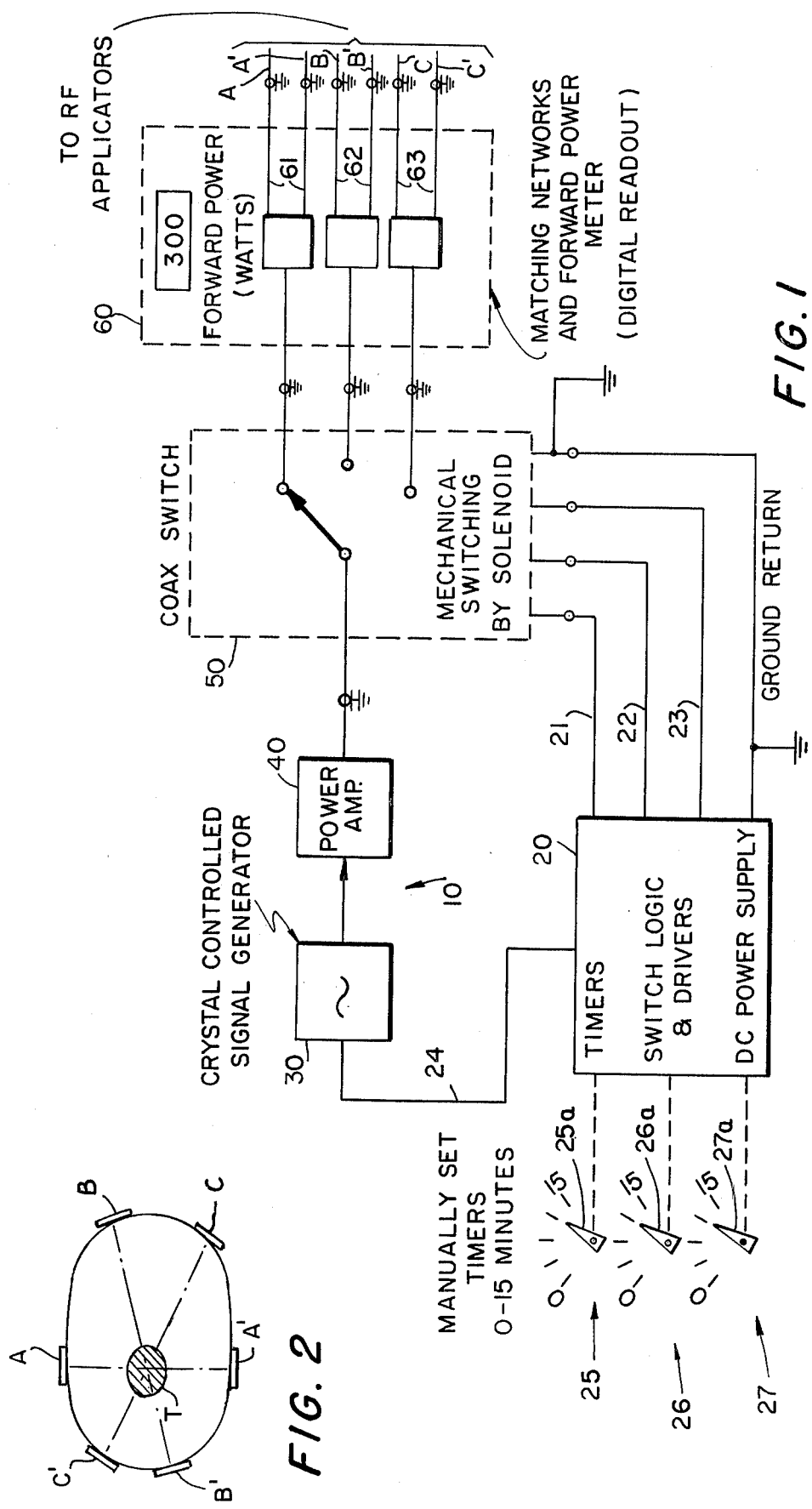

MULTI-PORTAL RADIOFREQUENCY GENERATOR

RELATED APPLICATIONS

The present application is a continuation-in-part of LeVeen application Ser. No. 686,300, filed May 14, 1976.

This invention relates to human and animal therapy involving the application of radiofrequency electromagnetic radiation and in particular provides an apparatus having utility in the application of R.F. energy to an interior situs within a human or animal.

BACKGROUND OF THE INVENTION

Methods and apparatus for the heating of animal tissue containing benign and malignant tumors and lesions without any apparent effect on the surrounding non-tumor tissue while necrosing or at least partially destroying the tumor mass are disclosed by LeVeen et al, JAMA 235:2198–2200(1976). An example of this is copending LeVeen patent application Ser. No. 643,661, filed Dec. 23, 1975, which describes the use of an R.F. generator attached to a single pair of electrode plates or discs which are placed in contact with the skin surface of the animal so that the submerged tumor mass is positioned in a field of R.F. energy set up between the pair of electrode plates. This apparatus works well, particularly with tumors which are near the surface and where high input of energy does not begin to pose a problem of skin surface heating and skin burn or irritation at the portal of entry of the energy.

However, in cases where a high level of energy is required over a longer period of treatment, up to several hours in some cases, a need for an apparatus which would maintain a constant level of R.F. energy input on the tumor target while at the same time reducing the surface tissue stress at the locus of contact between the skin of the patient and the electrode arose. This need was met by the design and manufacture of the hereinbelow described apparatus which comprises a plurality of sets of paired electrode plates. Each set of paired plates, i.e., applicators, are placed parallel to each other along an axis extending through the target tumor mass, but the sets are aligned on different axes, such that the portals of entry, the surfaces of the body against which the plates are positioned, differ. The various axes of paired plates of course intersect at the tumor mass within the body. The various sets of paired plates placed opposite each other operate under a timer control mechanism such that when R.F. energy is applied to one set of paired opposed electrode plates, the other sets of paired opposed electrodes are unenergized and inactive. When the first active set of electrodes is shut off by the timer, the next set automatically is activated and so on in sequence through the remaining sets of paired plates, activating one set at a time. In the preferred arrangement the length of time of actuation of each set of paired plates is controlled independently of the other sets, for example, by the provision of individual timing means associated with each set of paired plates through the control mechanism.

The operation of the device may be more fully understood by reference to the appended drawings in which:

FIG. 1 shows a block diagram the arrangement of the various component parts of the system; and FIG. 2 illustrates the application of the invention in therapeutic treatment of a tumor.

In FIG. 1 the reference numeral 10 generally designates a radiofrequency power generator for generating radiofrequency electromagnetic power having a frequency of 13.56 MHz. R.F. generator 10 basically includes a crystal controlled signal generator 30 the output of which is connected to a power amplifier 40 capable of output of up to a kilowatt or more at the frequency of 13.56 MHz supplied by signal generator 30.

The apparatus also includes a control mechanism 20 for controlling the operation of signal generator 30 and also for controlling the operation of a coaxial switch mechanism 50 connected to the output of power amplifier 40 for selectively coupling the output of power amplifier 40 to any of three output circuits 61, 62 and 63 thru matching networks, forward power meters and the like indicated generally by the reference numeral 60. Each output circuit 61, 62 and 63, as generally indicated in copending application Ser. No. 643,661, includes a pair of shielded output leads connected across the output of the R.F. generator, in the illustrated case through matching networks 60 and switch 50, which lead to a pair of applicators, in the illustrated case denoted by the reference numerals A and A' for output circuit 61, B and B' for output circuit 62 and C and C' for output circuit 63. Applicators A-A', B-B' and C-C' are intended to be placed generally parallel to each other in pairs such as pair A and A' with the tumor mass T located between them and with the electrodes placed flat against the surface of the body in intimate contact with it. Generally, in accordance with this invention the pairs of electrodes, such as A and A', associated with each output, such as circuit 61, as shown in FIG. 2, are arranged such that they are aligned perpendicularly to an axis extending through the tumor mass T which is to be treated. In addition the various pairs of electrodes are positioned such that the axes of alignment differ but all pass through and approximately intersect at the location of the tumor mass T.

Control mechanism 20 is a stepping switch, ring counter or the like designed when actuated to advance repetitively through a series of three positions. Control mechanism 20 is arranged with suitable timers, switch logic, driving mechanisms and power supply to connect power sequentially through output lines 21, 22 and 23 to operate coaxial switch 50 to connect the output of power amplifier 40 through matching networks and meters 60 to output circuit 61, output circuit 62 and output circuit 63, respectively, as indicated schematically in FIG. 1.

Control mechanism 20 also has an "off" position in which lines 21, 22 and 23 are inactivated and no connection is made between power amplifier 40 and any of output circuits 61, 62 and 63. Control mechanism 20 also, as indicated by line 24, is arranged to activate generator 30 when any of lines 21, 22 and 23 is activated. Control mechanism 20 further is provided with three associated timers 25, 26 and 27 which are manually programable for a time period from zero to 15 minutes. Timers 25, 26 and 27 are associated through control mechanism 20 each with one output circuit 21, 22 and 23, respectively, to control the length of time such circuit is actuated when control mechanism 20 is actuated to operate such circuits in sequence. Thus timer 25, for example, controls the length of time in which output circuit 21 is actuated, and power is therefore connected through switch 50 to output circuit 61.

In operation, referring the FIG. 2 electrodes A and A', B and B' and C and C' are placed on the body in intimate contact with the skin as described, for example, in application Ser. No. 643,661. More specifically, electrodes A—A' are placed on opposite sides of the body parallel to each other centered on a axis extending through the location of the tumor mass T be treated. Electrodes B—B' are similarly placed but centered on a different axis, and electrodes C—C' are also similarly placed but on yet a third axis all of which approximately intersect within tumor mass T.

The operator thus has three timer knobs 25a, 26a and 27a, each with an arrow to be set at a time scale of from 0 to 15 minutes which is set manually. If knob 25a is set at 15 minutes and 26a and 27a at zero setting control mechanism 20 will activate circuit 61 to operate for 15 minutes and then shut off. If, however, timer knob 25a is set at 15 minutes, timer knob 26a at 15 minutes and also timer knob 27a at 15 minutes, then when control mechanism 20 is activated the first circuit 61 will operate for 15 minutes and energize electrodes A and A'. Then in sequence switch 50 will deactivate circuit 61 and energize circuit 62 and its electrodes B and B' for 15 minutes. Following this interval switch 50 will deactivate circuit 62 and energize circuit 63 and its electrodes C and C' which are positioned at a different angle to the substrate and its submerged tumor T than either electrodes A—A' or B—B'.

The end result is a crossfire of the submerged tumor T from first electrodes A—A', then electrodes B—B' and finally electrodes C—C' on target but with a reduced skin contact time at any portal of entry of the input R.F. energy. This in a simplified version is how the present pre-timed sequence of multi-electrode energy sources operates. The basic idea for such a system is to prevent an over extension of the dwell time of any high power energy input system at a single locus on the skin or as referred to herein "portal of entry" of the R.F. radiation. The impedence matching networks are essentially convential and are designed to match line impedence with the impedence of the load between applicators. The forward power is typically in the range of 300–500 watts and this value is carefully monitored even though the present system permits a switch of the electrodes from one locus to another.

The logic network in control mechanism 20 is so arranged that it will switch time from line 21 to line 22 to line 23, and hence from circuit 61 to circuit 62 to circuit 63 in sequence at the end of the designated time interval as earlier set on timers 25, 26 and 27. If there is a zero setting on any timer it will switch in sequence past that point to the next time interval. Therefore, if 26 and 27 are set at zero timer 25 will be idefinitely recycled after its time has elapsed until the machine is turned off.

The switch logic of control mechanism 20, as indicated above, also controls by output 24 the output of the crystal controlled signal generator 30. This is necessary since the R.F. cannot be switched at high power output levels. Hence, the power output of signal generator 30 is momentarily cut off during the switching interval. When the output of 30 is temporarily interrupted the output from the power amplifier 40 falls to 0 making it possible to switch the R.F. at switch 50 from one coaxial cable to another.

I claim as my invention:

1. In an apparatus for the application of radio frequency electromagnetic energy to a biological substrate including generator means for generation of radio frequency electromagnetic power and applicator means connected to the radio frequency power output of said generator means for applying said power output of said generator means to a said biological substrate, the improvement in which said applicator means comprises a plurality of applicator pairs for setting up a radio frequency electromagnetic field therebetween when connected to said radio frequency generator means, switching means for coupling the power output of said radio frequency generator means selectively across each said pair, one pair at a time, and control means for actuating said generator means including means for actuating said switching means to couple said power output thereof to each of said applicator pairs in predetermined sequence.

2. The improvement according to claim 1 wherein said radio frequency power output coupled to each said applicator pair is greater than 200 watts.

3. An apparatus according to claim 1 in which said control means includes a plurality of timer means, each timer means being associated with the actuation of said switching means with a different set of said pair of applicators whereby the time of actuation of each said set of paired appalicators is separately controlled from each other set of paired applicators.

4. An apparatus according to claim 1 in which said control means operates to deactuate said generator means when actuating said switching means to change the coupling of the radio frequency power of said generator means from one to another of said sets of paired applicators.

* * * * *